United States Patent
Chin et al.

(10) Patent No.: US 6,181,963 B1
(45) Date of Patent: Jan. 30, 2001

(54) TRANSDERMAL ELECTROTRANSPORT DELIVERY DEVICE INCLUDING A CATHODIC RESERVOIR CONTAINING A COMPATIBLE ANTIMICROBIAL AGENT

(75) Inventors: Ivan W. Chin, Belmont, CA (US); Thomas O. Murdock, Vadnais Heights, MN (US); Michel J. N. Cormier, Mountain View, CA (US)

(73) Assignee: Alza Corporation, Mountain View, CA (US)

( * ) Notice: Under 35 U.S.C. 154(b), the term of this patent shall be extended for 0 days.

(21) Appl. No.: 09/433,615

(22) Filed: Nov. 2, 1999

Related U.S. Application Data (60) Provisional application No. 60/106,873, filed on Nov. 2, 1998.

(51) Int. Cl.[7] .................................................. A61N 1/30
(52) U.S. Cl. ............................................. 604/20; 607/152
(58) Field of Search ......................... 604/20, 21, 890.1; 607/115, 145, 152, 153

(56) References Cited

U.S. PATENT DOCUMENTS

| | | | |
|---|---|---|---|
| 4,585,652 | 4/1986 | Miller et al. | 424/83 |
| 5,023,085 | 6/1991 | Francoeur et al. | 424/449 |
| 5,047,007 | 9/1991 | McNichols | 604/20 |
| 5,169,384 | 12/1992 | Bosniak et al. | 604/20 |
| 5,298,017 | 3/1994 | Theeuwes et al. | 604/20 |
| 5,434,144 | 7/1995 | Kasting et al. | 514/76 |
| 5,624,415 | 4/1997 | Cormier et al. | 604/20 |
| 5,668,120 | 9/1997 | Shinoda et al. | 514/102 |
| 5,788,666 | 8/1998 | Atanasoska | 604/20 |

FOREIGN PATENT DOCUMENTS

| | | | |
|---|---|---|---|
| WO 95/27530 | 10/1995 | (WO) | A61N/1/30 |
| WO 96/39222 | 12/1996 | (WO) | A61N/1/30 |
| WO 96/39223 | 12/1996 | (WO) | A61N/1/30 |
| WO 96/39224 | 12/1996 | (WO) . | |
| WO 98/20869 | 5/1998 | (WO) | A61K/31/165 |

*Primary Examiner*—Sharon Kennedy
*Assistant Examiner*—Deborah Blyveis
(74) *Attorney, Agent, or Firm*—Owen J. Bates; Steven F. Stone (57) ABSTRACT

A transdermal electrotransport drug delivery device having an anode, a cathode and a source of electrical power electrically connected to the anode and the cathode. The cathode includes a cathodic electrode and a cathodic reservoir comprised of a housing composed of a polymeric material and an aqueous medium in contact with the housing. The aqueous medium includes i) a drug or an electrolyte salt or a mixture thereof and ii) a cetylpyridinium salt in an amount sufficient to inhibit microbial growth in the aqueous medium. The polymeric material is compatible with the cetylpyridinium salt. A process is also provided wherein when electric current flows from the source of electrical power so that the drug is transdermally delivered to the patient by electrotransport from the anodic reservoir, the cetylpyridinium salt is not transdermally delivered to the patient by electrotransport from the cathodic reservoir. A process for preparing a transdermal electrotransport drug delivery device is also provided.

26 Claims, 1 Drawing Sheet

FIG. 1

TRANSDERMAL ELECTROTRANSPORT DELIVERY DEVICE INCLUDING A CATHODIC RESERVOIR CONTAINING A COMPATIBLE ANTIMICROBIAL AGENT

This application claims benefit of Provisional Ser. No. 60/106,873, filed Nov. 2, 1998.

BACKGROUND OF THE INVENTION

A. Field of the Invention

The present invention relates to a transdermal electrotransport delivery device that includes a cathodic reservoir that contains a antimicrobial agent that is compatible with the material of the cathodic reservoir. The present invention further relates to a process for transdermally delivering a drug to a patient by electrotransport from a drug delivery device and a process for preparing a transdermal electrotransport delivery device.

B. Description of the Related Art

The transdermal delivery of drugs, by diffusion through the epidermis, offers improvements over more traditional delivery methods, such as subcutaneous injections and oral delivery. Transdermal drug delivery also avoids the hepatic first pass effect encountered with oral drug delivery. As used in the past, the term "transdermal" delivery, broadly encompasses the delivery of an agent through a body surface, such as the skin, mucosa, nails or other body surfaces (e.g., an organ surface) of an animal.

The skin functions as the primary barrier to the transdermal penetration of materials into the body and represents the body's major resistance to the transdermal delivery of beneficial agents such as drugs. To date, efforts have been concentrated on reducing the physical resistance or enhancing the permeability of the skin for the delivery of drugs by passive diffusion. Various methods of increasing the rate of transdermal drug flux have been attempted, most notably by using chemical flux enhancers.

Other approaches to increase the rates of transdermal drug delivery include the use of alternative energy sources such as electrical energy and ultrasonic energy. Electrically assisted transdermal delivery is also referred to as electrotransport. The term "electrotransport" as used herein refers generally to the delivery of a beneficial agent (i.e., a drug) through a membrane, such as skin, mucous membrane, nails or other body surfaces which is induced or aided by application of an electrical potential. For example, a beneficial agent may be introduced into the systemic circulation of a human body by electrotransport delivery through the skin. A widely used electrotransport process, referred to as electromigration (also called iontophoresis), involves the electrically induced transport of charged ions. Another type of electrotransport, referred to as electroosmosis, involves the flow of a liquid, which liquid contains the agent to be delivered, under the influence of an electric field. Still another type of electrotransport process, referred to as electroporation, involves the formation of transiently-existing pores in a biological membrane by the application of an electric field. An agent can be delivered transdermally either passively (i.e., without electrical assistance) or actively (i.e., under the influence of an electric potential). However, in any given electrotransport process, more than one of these processes, including at least some "passive" diffusion, may be occurring simultaneously to a certain extent. Accordingly, the term "electrotransport", as used herein, is given its broadest possible interpretation so that it includes the electrically induced or enhanced transport of at least one agent, which may be charged, uncharged, or a mixture thereof, whatever the specific mechanism or mechanisms by which the agent actually is transported.

Electrotransport delivery devices use at least two electrodes that are in electrical contact with some portion of the skin, nails, mucous membrane, or other surface of the body. One electrode, commonly called the "donor" electrode, is the electrode from which the agent is delivered into the body. The other electrode, typically termed the "counter" electrode, serves to close the electrical circuit through the body. For example, if the agent to be delivered is positively charged, i.e., a cation, then the anodic electrode is the donor electrode, while the cathodic electrode is the counter electrode which serves to complete the circuit. Alternatively, if an agent is negatively charged, i.e., an anion, the cathodic electrode is the donor electrode and the anodic electrode is the counter electrode. Additionally, both the anodic and cathodic electrodes may be considered donor electrodes if both anionic and cationic agent ions, or if uncharged dissolved agents, are to be delivered.

Furthermore, electrotransport delivery devices generally require at least one reservoir or source of the beneficial agent to be delivered to the body. Examples of such donor reservoirs include a pouch or cavity, a porous sponge or pad, and a hydrophilic polymer or a gel matrix. Such donor reservoirs are electrically connected to, and positioned between, the anodic or cathodic electrodes and the body surface, to provide a fixed or renewable source of one or more beneficial agents. Electrotransport devices also have an electrical power source such as one or more batteries. Typically, at any one time, one pole of the power source is electrically connected to the donor electrode, while the opposite pole is electrically connected to the counter electrode. Since it has been shown that the rate of electrotransport drug delivery is approximately proportional to the electric current applied by the device, many electrotransport devices typically have an electrical controller that controls the voltage and/or current applied through the electrodes, thereby regulating the rate of drug delivery. These control circuits use a variety of electrical components to control the amplitude, polarity, timing, waveform shape, etc. of the electric current and/or voltage supplied by the power source. See, for example, McNichols et al., U.S. Pat. No. 5,047,007.

A temperature variable and iontophoretic device for application to the body of a patient is described in Bosniak et al., U.S. Pat. No. 5,169,384. The device can selectively apply to or remove thermal energy from portions of a body of a patient as well as iontophoretically administer a compound. In various embodiments, the device is configured to be applied to the face or knee of a patient.

In a further development of electrotransport devices, hydrogels have become particularly favored for use as the drug and electrolyte reservoir matrices, in part, due to the fact that water is the preferred liquid solvent for use in electrotransport drug delivery due to its excellent biocompatibility compared with other liquid solvents such as alcohols and glycols. Hydrogels have a high equilibrium water content and can quickly absorb water. In addition, hydrogels tend to have good biocompatibility with the skin and mucosal membranes.

Electrotransport delivery devices are prepared, shipped and stored (or stored, shipped and stored), prescribed and then used. As a result, the devices must have components that have extended shelf lives that in some instances must comply with regulatory requirements. For instance, the U.S. Food and Drug Administration has shelf life requirements of from six to eighteen months for some materials. One complicating factor in achieving an extended shelf life is that the aqueous environment in the electrode reservoirs provides an excellent medium for microorganism growth. Accordingly, an antimicrobial agent can be incorporated in the aqueous medium of the electrode reservoirs to inhibit the proliferation of microorganisms.

A number of antimicrobial agents have been used in different environments. Known antimicrobial agents (sometimes referred to as biocides) include chlorinated hydrocarbons, organometallics, halogen-releasing compounds, metallic salts, organic sulfur compounds, quaternary ammonium compounds and phenolics. Illustrative compounds include sorbic acid, benzoic acid, methyl paraben and cetylpyridinium chloride. For instance, U.S. Pat. No. 5,434,144 describes topical compositions several of which include methyl paraben or cetylpyridinium salt.

In the context of electrotransport devices, U.S. Pat. No. 5,668,120 describes at column 8, lines 16–21 that preservatives, such as methyl paraben and cetylpyridinium chloride, can be optionally included in the liquid vehicle of the iontophoresis medium and several of the examples of the patent include such compounds. In addition, U.S. Pat. Nos. 4,585,652 and 5,788,666 disclose that cetylpyridinium chloride can be administered by iontophoresis while U.S. Pat. No. 5,298,017 describes a number of different types of materials which can be administered by electrotransport.

DISCLOSURE OF THE INVENTION

It has been discovered that various antimicrobial agents are absorbed into the polymeric material that constitutes the housing containing the aqueous medium thereby reducing the effectiveness of the antimicrobial agent in the aqueous medium. It has also been determined that the effectiveness of the antimicrobial agent can be maintained by avoiding transdermal delivery of the antimicrobial agent to a patient by electrotransport while a drug is being delivered to the patient by electrotransport.

Accordingly, one aspect of the present invention relates to a transdermal electrotransport drug delivery device comprised of an anode, a cathode and a source of electrical power electrically connected to the anode and the cathode, the cathode including a cathodic electrode and a cathodic reservoir comprised of a housing composed of a polymeric material and an aqueous medium in contact with the housing, said aqueous medium comprised of i) a drug or an electrolyte salt or a mixture thereof and ii) a cetylpyridinium salt in an amount sufficient to inhibit microbial growth in the aqueous medium wherein said polymeric material is compatible with the cetylpyridinium salt.

In a further aspect, the present invention relates to a process for transdermally delivering a drug to a patient by electrotransport from a drug delivery device comprised of an anode, a cathode and a source of electrical power electrically connected to the anode and the cathode, the anode including an anodic electrode and an anodic reservoir that contains a drug and the cathode including a cathodic electrode and a cathodic reservoir composed of a polymeric material and containing an aqueous medium comprised of i) an electrolyte salt and ii) a cetylpyridinium salt in an amount sufficient to inhibit microbial growth in the aqueous medium, said polymeric material being compatible with the cetylpyridinium salt, said process comprising providing electric current from the source of electrical power so that the drug is transdermally delivered to the patient by electrotransport from the anodic reservoir and so that the cetylpyridinium salt is not transdermally delivered to the patient by electrotransport from the cathodic reservoir.

In a still further aspect, the present invention relates to a process of preparing a transdermal electrotransport drug delivery device. The process comprises preparing an aqueous medium comprised of i) a drug or an electrolyte salt or a mixture thereof and ii) a cetylpyridinium salt in an amount sufficient to inhibit microbial growth in the aqueous medium; and placing the aqueous medium in the cathodic reservoir of a device comprised of an anode, a cathode and a source of electrical power electrically connected to the anode and the cathode, the cathode including a cathodic electrode and a cathodic reservoir comprised of a housing composed of a polymeric material whereby the aqueous medium is in contact with the housing of the cathodic reservoir and wherein said polymeric material is selected so that it is compatible with the cetylpyridinium salt.

MODES FOR CARRYING OUT THE INVENTION

As noted above, one aspect of the present invention relates to a transdermal electrotransport drug delivery device which is designed to deliver a drug to a patient through the skin or a mucosal membrane. The transdermal electrotransport drug delivery device is comprised of an anode, a cathode and a source of electrical power electrically connected to the anode and the cathode, the cathode including a cathodic electrode and a cathodic reservoir comprised of a housing composed of a polymeric material and an aqueous medium in contact with the housing, said aqueous medium comprised of i) a drug or an electrolyte salt or a mixture thereof and ii) a cetylpyridinium salt in an amount sufficient to prevent microbial growth in the aqueous medium and said polymeric material being compatible with the cetylpyridinium salt.

The cetylpyridinium salt used in the present invention is a highly effective antimicrobial agent and can kill or at least inhibit the growth of a number of microorganisms, both bacteria and fungi. The antimicrobial effectiveness in the cathodic reservoir is especially pronounced in view of a pH range of from about 3 to about 7.5, preferably from about 3.5 to about 6.5, which is present in the aqueous medium of the cathodic reservoir and, at the lower levels of these pH ranges, can itself provide a certain level of antibacterial activity.

The cetylpyridinium salt is present in an amount sufficient to inhibit microbial growth in the aqueous medium. In general, the aqueous medium contains at least about 0.005% by weight of the cetylpyridinium salt. More specifically, the aqueous medium contains from about 0.005% to about 2% by weight of the cetylpyridinium salt and preferably contains from about 0.01% to about 1% by weight of the cetylpyridinium salt. In calculating the weight of the aqueous medium, the amount of the gel matrix (to the extent that one is present) is not included.

The cetylpyridinium salt can be a cetylpyridinium halide salt or a mixture thereof. The cetylpyridinium salt is preferably a cetylpyridinium halide salt and cetylpyridinium chloride is especially preferred.

The cetylpyridinium salt can be used in the cathodic reservoir of substantially any transdermal electrotransport delivery device. In general, an electrotransport device provides the transdermal delivery of the drug by electrically induced or enhanced transport of the drug in a form which may be charged, uncharged, or a mixture thereof, whatever the specific mechanism or mechanisms by which the drug is transported. Electrotransport is based on electrical potential to increase the flux or rate of drug delivery compared to passive (i.e., non-electrically assisted) transdermal delivery systems which deliver a drug through the skin solely by diffusion. An especially applicable mechanism is by iontophoresis where the drug is administered in charged (ionized) form. As further discussed above, when the drug is to be administered as a cation, the drug is originally present in an anodic reservoir of the drug delivery device. On the other hand, when the drug is to be administered as an anion, the drug is originally present in a cathodic reservoir of the drug delivery device. It is also possible to have drugs in both cationic and anionic form that are simultaneously delivered from the anodic reservoir and cathodic reservoir, respectively.

Any drug which can be transdermally delivered by electrotransport can be used with the present invention including, without limitation, anti-infectives such as antibiotics and antiviral agents; analgesics such as fentanyl, sufentanil, and buprenorphine, and analgesic combinations; anesthetics; anorexics; antiarthritics; antiasthmatic agents such as terbutaline; anticonvulsants; antidepressants; antidiabetics agents; antidiarrheals; antihistamines; antiinflammatory agents; antimigraine preparations; antimotion sickness preparations such as scopolamine and ondansetron; antinauseants; antineoplastics; antiparkinsonism drugs; antipruritics; antipsycbotics; antipyretics; antispasmodics including gastrointestinal and urinary; anticholinergics; sympathomimetrics; xanthine derivatives; cardiovascular preparations including calcium channel blockers such as nifedipine; beta-agonists such as dobutamine and ritodrine; beta blockers; antiarrythmics; antihypertensives such as atenolol; ACE inhibitors such as ranitidine; diuretics; vasodilators including general, coronary, peripheral and cerebral; central nervous systems stimulants; cough and cold preparations; decongestants; diagnostics; hormones such as parathyroid hormones; hypnotics; immunosuppressives; muscle relaxants; parasympatholytics; parasympathomimetrics; prostaglandins; proteins; peptides; psychostimulants; sedatives and tranquilizers.

More specific drugs include baclofen, beclomethasone, betamethasone, buspirone, cromolyn sodium, diltiazem, doxazosin, droperidol, encainide, fentanyl, hydrocortisone, indomethacin, ketoprofen, lidocaine, methotrexate, metoclopramide, miconazole, midazolam, nicardipine, piroxicam, prazosin, scopolamine, sufentanil, terbutaline, testosterone, tetracaine, and verapamil.

The present invention is also useful in the controlled delivery of peptides, polypeptides, proteins, or other macromolecules difficult to deliver transdermally or transmucosally because of their size. These macromolecular substances typically have a molecular weight of at least about 300 daltons, and more typically, a molecular weight in the range of about 300 to 40,000 daltons. Examples of peptides and proteins which may be delivered using the device of the present invention include, without limitation, LHRH, LHRH analogs such as buserelin, goserelin, gonadorelin, naphrelin, naturetin, leuprolide, GHRH, GHRF, insulin, insulinotropin, heparin, calcitonin, octreotide, endorphin, TRH, NT-36 (chemical name; N-[[(s)4-oxo-2-azetidinyl]carbonyl]L-histidyl-L-prolinamide], liprecin, pituitary hormones (e.g., HGH, HMG, HCG, desmopressin acetate), follicle luteoids, -ANF, growth factor releasing factor (GFRF), -MSH, somatostatin, bradykinin, somatotropin, platelet-derived growth factor, asparaginase, bleomycin sulfate, chymopapain, cholecystokinin, chorionic gonadotropin, corticotropin (ACTH), erythropoietin, epoprostenol (platelet aggregation inhibitor), glucagon, hirulog, hyaluronidase, interferon, interleukin-2, meno-tropins (urofollitropin (FSH) and LH), oxytocin, streptokinase, tissue plasminogen activator, urokinase, vasopressin, desmopressin, ACTH analogs, ANP, ANP clearance inhibitors, angiotensin II antagonists, antidiuretic hormone agonists, antidiuretic hormone antagonists, bradykinin antagonists, CD4, ceredase, CSF S, enkephalins, FAB fragments, IgE peptide suppressors, IGF-1, neurotrophic factors, colony stimulating factors, parathyroid hormone and agonists, parathyroid hormone antagonists, prostaglandin antagonists, pentigetide, protein C, protein S, renin inhibitors, thymosin alpha-1, thrombolytics, TNF, vaccines, vasopressin antagonist analogs, alpha-1 antitrypsin (recombinant), and TGF-beta.

Particularly preferred drugs which can be delivered by the device and process of the present invention are fentanyl and sufentanil which are synthetic opiates that are characterized by their rapid analgesic effect and short duration of action. They are extremely potent and are estimated to be 80 and 800 times, respectively, more potent than morphine. Both drugs are amine compounds and hence are weak bases whose major fraction is in cationic form in an acidic aqueous medium. When fentanyl or sufentanil is used as the drug to be administered from the anodic reservoir, the cathodic reservoir is typically substantially drug free. Examples of transdermal electrotransport fentanyl and sufentanil delivery devices are disclosed in WO 96/39222; WO 96/39223; and WO 96/39224, the disclosures of which are incorporated by reference.

When fentanyl is used in the device, it is typically used in the form of acid addition salt, particularly the chloride salt, and the initial concentration in the aqueous medium of the anodic reservoir (i.e., before any drug is administered to the patient) is from about 10 to about 50 mg/ml, preferably from about 20 to about 55 mg/ml based on the number of moles of fentanyl salt contained in the donor reservoir, not the equivalent number of moles of fentanyl free base. In addition, the concentration is based on the volume of the liquid solvent, not on the total volume of the reservoir. In other words, the concentration does not include the volume of the reservoir which is represented by the reservoir matrix (e.g., the hydrogel or other matrix material).

In the context of the present invention, fentanyl is preferred over sufentanil. At a concentration of at least 5.7 mg/mL in the substantially neutral pH environment of the anodic reservoir, the fentanyl can provide antimicrobial properties against microorganisms such as *S. aureus, E. Coli, P. aeruginosa, B. pumilus* spores and *C. albicans*. At this concentration, the fentanyl also inhibits the growth of other microorganisms, such as *A. niger,* and is cidal for this fungus at concentrations on the order of 22.7 mg/mL. Accordingly, when fentanyl or a drug with similar antimicrobial properties is used as the drug to be administered to the patient from the anodic reservoir, the anodic reservoir need not contain a separate antimicrobial agent.

The cathodic electrode and the anodic electrode are comprised of electrically conductive material such as a metal. For example, the electrodes may be formed from a metal foil, a metal screen, on metal deposited or painted on a suitable backing or by calendaring, film evaporation, or by mixing the electrically conductive material in a polymer binder matrix. Examples of suitable electrically conductive materials include carbon, graphite, silver, zinc, aluminum, platinum, stainless steel, gold and titanium. For example, as noted above, the anodic electrode may be composed of silver which is also electrochemically oxidizable. The cathodic electrode may be composed of carbon and electrochemically reducible silver chloride. Silver is preferred over other metals because of its relatively low toxicity to mammals. Silver chloride is preferred because the electrochemical reduction reaction occurring at the cathode (AgCl+e$^-$ Ag+Cl$^-$) produces chloride ions which are prevalent in, and non-toxic to, most animals.

Alternatively, electrodes may be formed of a polymer matrix containing a conductive filler such as a metal powder, powdered graphite, carbon fibers, or other known electrically conductive filler material. The polymer based electrodes may be made by mixing the conductive filler in a polymer matrix, preferably a mixture of hydrophilic and hydrophobic polymers. The hydrophobic polymers provide structural integrity, while the hydrophilic polymers may enhance ion transport. For example, zinc powder, silver powder, powdered carbon, carbon fibers and mixtures thereof can be mixed in a hydrophobic polymer matrix, with the preferred amount of conductive filler being within the range of about 30 to about 90 volume percent, the remainder being the polymer matrix or other inert additives.

The source of electrical power electrically connected to the anode and the cathode can be of any variety. For instance, if the counter and donor electrodes are of dissimilar metals or have different half cell reactions, it is possible for the system to generate its own electrical power. Typical materials which provide a galvanic couple include a zinc donor electrode and a silver chloride counter electrode. Such a combination will produce a potential of about one volt. When a galvanic couple is used, the donor electrode and counter electrode are integral portions of the power generating process. Such a galvanic couple powered system, absent some controlling means, activates automatically when body tissue and/or fluids form a complete circuit with the system. There exist numerous other examples of galvanic couple systems potentially useful in the present invention.

In some instances it may be necessary to augment the power supplied by the galvanic electrode couple. This may be accomplished with the use of a separate electrical power source. Such a power source is typically a battery or plurality of batteries, connected in series or in parallel, and positioned between the cathodic electrode and the anodic electrode such that one electrode is connected to one pole of the power source and the other electrode is connected to the opposite pole. Commonly, one or more 3 volt button cell batteries, are suitable to power electrotransport devices. A preferred battery is a 3 volt lithium button cell battery.

The power source may include electronic circuitry for controlling the operation of the electrotransport device. Thus, the power source may include circuitry designed to permit the patient to manually turn the system on and off, such as with an on demand medication regime, or to turn the system on and off at some desired periodicity, for example, to match the natural or circadian patterns of the body. In addition, the control means can limit the number of doses that can be administered to the patient. A relatively simple controller or microprocessor could control the current as a function of time or could generate complex current waveforms such as pulses or sinusoidal waves. The control circuitry may also include a biosensor and some type of feedback system which monitors biosignals, provides an assessment of therapy, and adjusts the drug delivery accordingly. A typical example is the monitoring of the blood sugar level for controlled administration of insulin.

The aqueous medium in the cathodic reservoir, as well as the aqueous medium that is typically in the anodic reservoir, can be any material adapted to absorb and hold a sufficient quantity of liquid therein in order to permit transport of agent therethrough by electrotransport. For example, gauzes, pads or sponges composed of cotton or other absorbent fabric, both natural and synthetic, may be used. More preferably, the aqueous media are composed, at least in part, of one or more hydrophilic polymers. Hydrophilic polymers are typically preferred because water is the preferred ion transport medium and hydrophilic polymers have a relatively high equilibrium water content. Most preferably, the aqueous media in reservoirs are polymer matrices composed, at least in part, of hydrophilic polymer. Insoluble hydrophilic polymer matrices are preferred over soluble hydrophilic polymers in view of their structural properties (e.g., less swelling upon absorbing water).

The aqueous media can be a gel wherein the gel is formed of a hydrophilic polymer which is insoluble or soluble in water. Such polymers can be blended with the components in any ratio, but preferably represent from a few percent up to about 50 percent by weight of the reservoir. The polymers can be linear or crosslinked. Suitable hydrophilic polymers include copolyesters such as HYTREL® (DuPont De Nemours & Co., Wilmington, Del.), polyvinylpyrrolidones, polyvinyl alcohol, polyethylene oxides such as POLYOX (Union Carbide Corp.), CARBOPOL® (BF Goodrich of Akron, Ohio), blends of polyoxyethylene or polyethylene glycols with polyacrylic acid such as POLYOX® blended with CARBOPOL®, polyacrylamide, KLUCEL®, cross-linked dextran such as SEPHADEX® (Pharmacia Fine Chemicals, AB, Uppsala, Sweden), WATER LOCK® (Grain Processing Corp., Muscatine, Iowa) which is a starch-graft-poly(sodium acrylate-co-acrylamide) polymer, cellulose derivatives such as hydroxyethyl cellulose, hydroxypropylmethylcellulose, low-substituted hydroxypropylcellulose, and cross-linked Na-carboxymethylcellulose such as Ac-DiSol (FMC Corp., Philadelphia, Pa.), hydrogels such as polyhydroxyethyl methacrylate (National Patent Development Corp.), natural gums, chitosan, pectin, starch, guar gum, locust bean gum, and the like, along with blends thereof. Of these, polyvinyl alcohols are preferred in an amount ranging from about 5 to about 35% by weight, preferably from about 19 to about 23% by weight of the contents of the reservoir. This list is merely exemplary of the materials suited for use in this invention. Other suitable hydrophilic polymers can be found in J. R. Scott & W. J. Roff, Handbook of Common Polymers (CRC Press, 1971), which is hereby incorporated by reference.

Optionally, a hydrophobic polymer may be present, to improve structural integrity. Preferably the hydrophobic polymer is heat fusible, in order to enhance the lamination to adjacent layers. Suitable hydrophobic polymers include, but are not limited to, polyisobutylenes, polyethylene, polypropylene, polyisoprenes and polyalkenes, rubbers, copolymers such as KRATON®, polyvinylacetate, ethylene vinyl acetate copolymers, polyamides such as nylons, polyurethanes, polyvinylchloride, acrylic or methacrylic resins such as polymers of esters of acrylic or methacrylic acid with alcohols such as n-butanol, 1-methyl pentanol, 2-methyl pentanol, 3-methyl pentanol, 2-ethyl butanol isooctanol, n-decanol, alone or copolymerized with ethylenically unsaturated monomers such as acrylic acid, methacrylic acid, acrylamide, methacrylamide, N-alkoxymethyl acrylamides, N-alkoxymethyl methacrylamides, N-tertbutylacrylamide, itaconic acid, N-branched alkyl maleamic acids, wherein the alkyl group has 10–24 carbon atoms, glycol diacrylates, and blends thereof. Most of the above-mentioned hydrophobic polymers are heat fusible. However, the materials used in the cathodic reservoir should be selected so that they are compatible with the cetylpyridinium salt.

The media in the anodic and cathodic reservoirs may be formed by blending the desired drug, electrolyte, or other component(s), with an inert polymer by such processes as melt blending, solvent casting, or extrusion. Typically, the anodic reservoir medium contains a drug to be delivered, while the cathodic reservoir medium contains an electrolyte, that is typically a biocompatible salt such as sodium chloride and the cetylpyridinium salt. The presence of the cetylpyridinium salt in the cathodic reservoir is advantageous because upon ionization, the cetylpyridinium cation is not delivered to the patient by electrotransport when electric current is provided in the device.

In addition to the drug and electrolyte, the anodic and cathodic reservoirs may also contain other conventional materials such as inert fillers and the like. For instance, the cathodic reservoir may contain from about 0.01 to about 1.0% by weight of an electrolyte salt, such as sodium chloride, from about 0.1 to about 1.0% by weight of citric acid or a comparable material and from about 0.1 to about 1.0% by weight of trisodium citrate dihydrate or a comparable material wherein the citric acid and the trisodium citrate dihydrate function as a buffer system.

In addition to a cationic drug, water and the hydrogel, the anodic reservoir may contain flux enhancers as disclosed in U.S. Pat. No. 5,023,085, buffers as disclosed in U.S. Pat. No. 5,624,415, halide resins as disclosed in WO 95/27530 and other known excipients. Specific additional components include sodium EDTA in an amount of from about 0.01 to about 1.0% by weight or L-histidine or L-histidine HCl in an amount of from about 0.1 to about 2.5% by weight.

Furthermore, one or more rate controlling membranes as disclosed in U.S. Pat. Nos. 5,080,646 and 5,147,296 may be placed between the donor reservoir and the body surface for controlling the rate at which the agent is delivered or limiting passive agent delivery when the power source is in an "off" mode.

Figure 1:
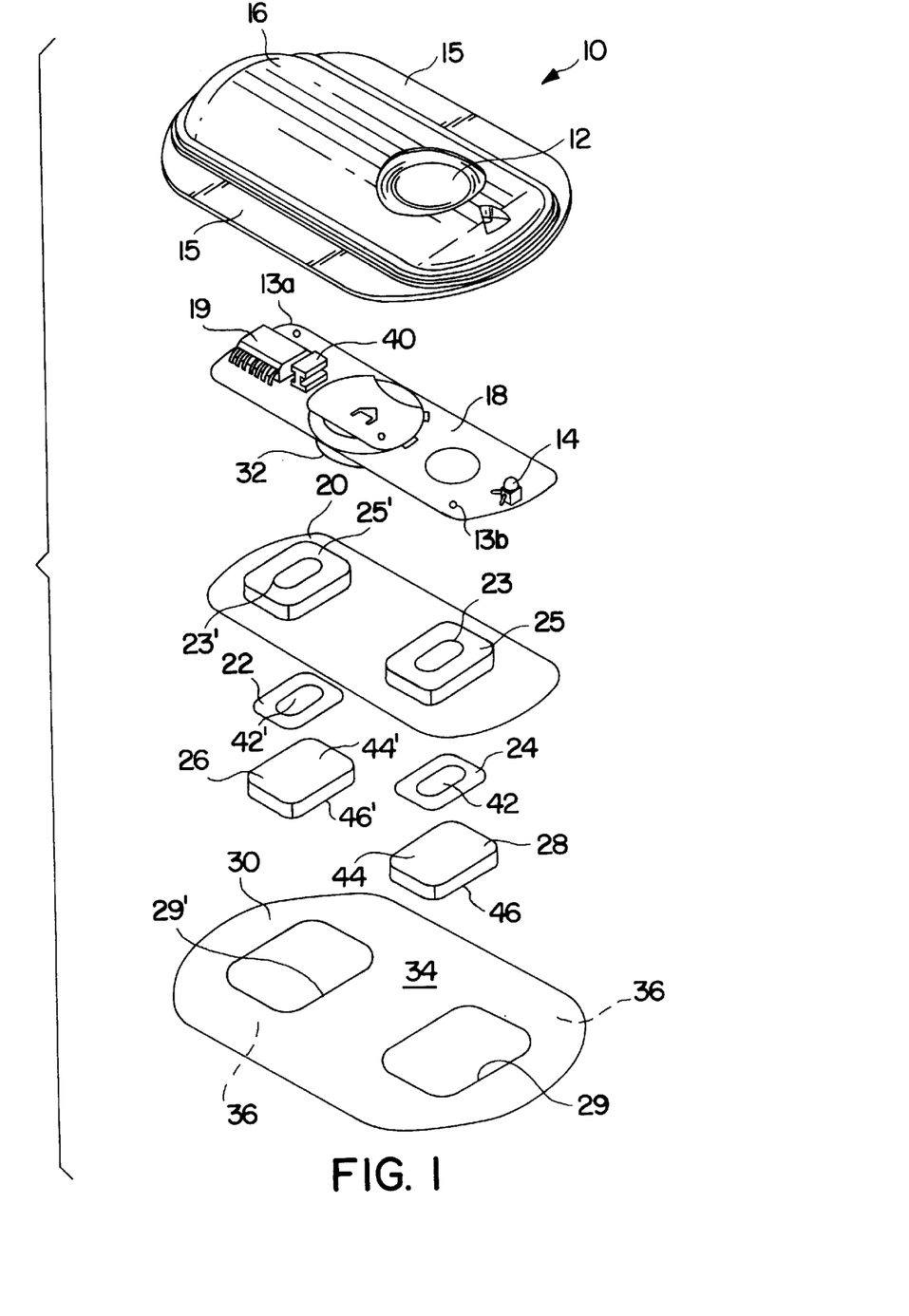
FIG. 1 is a perspective exploded view of an electrotransport drug delivery device in accordance with one embodiment of the present invention.

Reference is now made to FIG. 1 which depicts an exemplary electrotransport device which can be used in accordance with the present invention. FIG. 1 shows a perspective exploded view of an electrotransport device 10 having an activation switch in the form of a push button switch 12 and a display in the form of a light emitting diode (LED) 14. Device 10 comprises an upper housing 16, a circuit board assembly 18, a lower housing 20, anodic electrode 22, cathodic electrode 24, anodic reservoir 26, cathodic reservoir 28 and skin-compatible adhesive 30. Upper housing 16 has lateral wings 15 which assist in holding device 10 on a patient's skin. Upper housing 16 is preferably composed of an injection moldable elastomer (e.g., ethylene vinyl acetate).

Printed circuit board assembly 18 comprises an integrated circuit 19 coupled to discrete electrical components 40 and battery 32. Printed circuit board assembly 18 is attached to housing 16 by posts (not shown) passing through openings 13a and 13b, the ends of the posts being heated/melted in order to heat weld the circuit board assembly 18 to the housing 16. Lower housing 20 is attached to the upper housing 16 by means of adhesive 30, the upper surface 34 of adhesive 30 being adhered to both lower housing 20 and upper housing 16 including the bottom surfaces of wings 15.

Shown (partially) on the underside of printed circuit board assembly 18 is a battery 32, which is preferably a button cell battery and most preferably a lithium cell. Other types of batteries may also be employed to power device 10.

The circuit outputs (not shown in FIG. 1) of the circuit board assembly 18 make electrical contact with the electrodes 24 and 22 through openings 23,23' in the depressions 25,25' formed in lower housing, by means of electrically conductive adhesive strips 42,42'. Electrodes 22 and 24, in turn, are in direct mechanical and electrical contact with the top sides 44',44 of reservoirs 26 and 28. The bottom sides 46',46 of reservoirs 26,28 contact the patient's skin through the openings 29',29 in adhesive 30.

Upon depression of push button switch 12, the electronic circuitry on circuit board assembly 18 delivers a predetermined DC current to the electrodes/reservoirs 22,26 and 24,28 for a delivery interval of predetermined length, e.g., about 10–20 minutes. Preferably, the device transmits to the user a visual and/or audible confirmation of the onset of the drug delivery, or bolus, interval by means of LED 14 becoming lit and/or an audible sound signal from, e.g., a "beeper". Analgesic drug, e.g. fentanyl or sufentanil, is then delivered through the patient's skin, e.g., on the arm, for the predetermined delivery interval. In practice, a user receives feedback as to the onset of the drug delivery interval by visual (LED 14 becomes lit) and/or audible signals (a beep from a "beeper").

Anodic electrode 22 is preferably comprised of silver and cathodic electrode 24 is preferably comprised of carbon and silver chloride loaded in a polymer matrix material such as polyisobutylene. Both reservoirs 26 and 28 are preferably composed of polymer hydrogel materials as described herein. Electrodes 22, 24 and reservoirs 26, 28 are retained by lower housing 20. For fentanyl and sufentanil salts, the anodic reservoir 26 is the "donor" reservoir which contains the drug and the cathodic reservoir 28 contains a biocompatible electrolyte and the cetylpyridinium salt. If the electrode material is composed of materials which may absorb the cetylpyridinium salt, an ion exchange membrane can be located between the electrode 24 and the reservoir 28. Thus, for instance, an anion exchange membrane (not shown in FIG. 1), such as a SYBRON® or RAIPORE® anion exchange membrane, can be located between the cathodic electrode 24 and the cathodic reservoir 28 so that the cetylpyridinium cations will not penetrate through such membrane and therefore will not contact the cathodic electrode.

The push button switch 12, the electronic circuitry on circuit board assembly 18 and the battery 32 are adhesively "sealed" between upper housing 16 and lower housing 20. Upper housing 16 is preferably composed of rubber or other elastomeric material. Lower housing 20 is composed of polymeric sheet material which can be easily molded to form depressions 25,25' and cut to form openings 23,23'. The lower housing, particularly the portions containing anodic reservoir 26 and cathodic reservoir 28, is composed of a polymeric material. The polymeric material is compatible with cetylpyridinium salt so that the cetylpyridinium salt is substantially not absorbed into the polymeric material. Suitable polymeric materials include polyethylene terephthalate, polyethylene terephthalate modified with cyclohexane dimethylol (referred to as polyethylene terephthalate glycol or PETG) that renders the polymer more amorphous, polypropylene and mixtures thereof. Preferred polymeric materials are polyethylene terephthalate and PETG which are both commercially available and PETG is most preferred. A suitable PETG is available from Easan Chemical Products, Inc. under the designation KODAR® PETG copolyester 6763.

The assembled device 10 is preferably water resistant (i.e., splash proof and is most preferably waterproof. The system has a low profile that easily conforms to the body thereby allowing freedom of movement at, and around, the wearing site. The anodic drug reservoir 26 and the cathodic reservoir 28 are located on the skin-contacting side of device 10 and are sufficiently separated to prevent accidental electrical shorting during normal handling and use.

The device 10 adheres to the patient's body surface (e.g., skin) by means of a peripheral adhesive 30 which has upper side 34 and body-contacting side 36. The adhesive side 36 has adhesive properties which assures that the device 10 remains in place on the body during normal user activity, and yet permits reasonable removal after the predetermined (e.g., 24 hour) wear period. Upper adhesive side 34 adheres to lower housing 20 and retains the electrodes and drug reservoirs within housing depressions 25,25' as well as retains lower housing 20 attached to upper housing 16. The device is also usually provided with a release liner (not shown) that is initially attached to body-contacting side 36 of adhesive 30 and removed prior to attachment to the patient. The release liner is typically siliconized polyethylene ethylene terephthalate so that the cetylpyridinium salt also is compatible with this material.

The push button switch 12 is located on the top side of device 10 and is easily actuated through clothing. A double press of the push button switch 12 within a short period of time, e.g., three seconds, is preferably used to activate the device 10 for delivery of drug, thereby minimizing the likelihood of inadvertent actuation of the device 10.

Upon switch activation an audible alarm signals the start of drug delivery, at which time the circuit supplies a predetermined level of DC current to the electrodes/reservoirs for a predetermined (e.g., 10 minute) delivery interval. The LED 14 remains "on" throughout the delivery interval indicating that the device 10 is in an active drug delivery mode. The battery preferably has sufficient capacity to continuously power the device 10 at the predetermined level of DC current for the entire (e.g., 24 hour) wearing period. The integrated circuit 19 can be designed so that a predetermined amount of drug is delivered to a patient over a predetermined time and then ceases to operate until the switch is activated again and that after a predetermined number of doses has been administered, no further delivery is possible despite the presence of additional drug in the donor reservoir.

The material of the cathodic reservoir is selected so as to be compatible with the cetylpyridinium salt so that the antimicrobial effectiveness of the cetylpyridinium salt within the reservoir can be maintained even over an extended period such as can be encountered during shipping and storage or storage, shipping and storage prior to use of the transdermal electrotransport drug delivery device. This means that the material containing the aqueous medium of the cathodic reservoir, such as the lower housing of the device illustrated in FIG. 1, is selected such that it will not absorb substantial quantities of the cetylpyridinium salt that would reduce its antimicrobial effectiveness in the cathodic reservoir. Such material can also be used for the release liner (not shown) that is typically placed on the body-contacting surface 36 of peripheral adhesive 30. As used in the context of the present invention, the term "compatible" means that the material will not absorb a substantial amount of cetylpyridinium salt from the aqueous medium upon storage. To determine if a polymeric material is compatible with the cetylpyridinium salt, one can prepare an aqueous solution of the cetylpyridinium salt at a concentration of 0.1 mg/ml, immerse a sample of the polymeric material for four weeks at 25° C. and determine the amount of cetylpyridinium salt that is absorbed by the polymeric material by HPLC. If the amount of absorbed cetylpyridinium salt is less than 0.25 mg per gram of polymeric material, preferably less than 0.10 mg per gram of the polymeric material, most preferably less than 0.025 mg per gram of the polymeric material, the polymeric material can be considered to be compatible with the cetylpyridinium salt.

As indicated above, suitable polymeric materials that can be used to form the cathodic reservoir include polyethylene terephthalate, polyethylene terephthalate modified with cyclohexane dimethylol, polypropylene and mixtures thereof. Preferably, the material is polyethylene terephthalate or polyethylene terephthalate modified with cyclohexane dimethylol. The polymeric materials can be formed into the desired shape (e.g., the form of the lower housing) by hot molding or any other suitable technique.

The aqueous medium to be contained in the anodic reservoir can be prepared in accordance with any conventional technique. For instance, when the aqueous medium is a hydrogel formulation, it can be composed of from about 10 to about 30% by weight of polyvinyl alcohol, from about 0.1 to about 0.4% by weight of buffer, and the desired amount of drugs, such as fentanyl or sufentanil salt, particularly the hydrochloride salt. The remainder is water and other conventional ingredients. The hydrogel formulation can be prepared by mixing all ingredients, including the fentanyl or sufentanil salt, in a single vessel at an elevated temperature of from about 90 to about 95° C. for at least about 0.5 hour. The hot mixture is then poured into a foam mold and stored at a freezing temperature of about −35° C. for a period of time (e.g., overnight) sufficient to cross-link the polyvinyl alcohol. Upon warming to ambient temperature, a tough elastomeric gel is obtained suitable for placement in the anodic reservoir of the transdermal electrotransport delivery device.

The aqueous medium to be contained in the cathodic reservoir can also be prepared in accordance with any conventional technique. For instance, when the aqueous medium is a hydrogel formulation, it can be composed of from about 10 to about 30% by weight of polyvinyl alcohol and ingredients, such as sodium chloride, trisodium citrate, citric acid and the cetylpyridinium salt in the amounts described previously, with the balance being water. The hydrogel formulation can be prepared by mixing all ingredients and utilizing the procedure described with respect to the preparation of the hydrogel formulation used in the anodic reservoir.

The various aspects of the present invention can be understood from the following examples and comparative examples. It is to be understood, however, that the present invention is not limited by the representative embodiments shown in the examples.

EXAMPLE 1

To illustrate the antimicrobial effectiveness of the cetylpyridinium salt of the present invention, cathodic hydrogel formulations were made containing 0.01%, 0.02% and 0.03% cetylpyridinium chloride with three bacterial species, one yeast species, one mold species (these microorganisms are specified for the *Antimicrobial Preservative Effectiveness Test*) and one environment mold species. All percentages in this example are percent by weight unless otherwise noted. The viability of the inocula on the cathodic hydrogels was assayed in accordance with an *Antimicrobial Effectiveness Test*, which is generated in reference to and in compliance with those methods described in U.S. Pharmacopoeia 23 <51> *Antimicrobial Preservatives-Effectiveness;* British Pharmacopoeia (BP) Appendix XVI C *Efficacy of Antimicrobial Preservation;* and European Pharmacopoeia (EP) VIII.15 *Efficacy of Antimicrobial Preservation.*

The microorganisms used were as follows:
Bacteria
*Staphylococcus aureus* ATCC 6538
*Escherichia coli* ATCC 8739
*Pseudomonas aeruginosa* ATCC 9027
Yeast
*Candida albicans* ATCC 10231
Mold
*Aspergillus niger* ATCC 16404
Environmental Isolate
*Cladosporium species* (environmental isolate)
The formulations used in the tests are as follows:

|  | Formula I | Formula II | Formula III |
| --- | --- | --- | --- |
| Purified Water, USP | 80.28% | 80.27% | 80.26% |
| washed polyvinyl alcohol | 19.00% | 19.00% | 19.00% |
| sodium chloride, USP | 0.10% | 0.10% | 0.10% |
| trisodium chloride | 0.37% | 0.37% | 0.37% |
| citric acid, USP | 0.24% | 0.24% | 0.24% |
| cetylpyridinium chloride | 0.01% | 0.02% | 0.03% |
| pH | 4.5 | 4.5 | 4.5 |

Samples of the hydrogel formulation of Formulation 1 were prepared by adding into a 250 mL jacketed glass beaker 80.28 g USP purified water; 0.10 g sodium chloride, USP; 0.37 g trisodium citrate; 0.24 g citric Acid and 0.01 g cetylpyridinium chloride. The resulting mixture was stirred for 5 to 10 minutes with a glass stirring rod and the salts were completely dissolved. Washed poly(vinyl alcohol), 19.00 g, was added to the beaker and a rubber stopper equipped with a thermocouple thermometer and a glass stirring rod with a Delrin paddle was inserted into the mouth of the beaker. The mixture was warmed to 90 to 95° C. while stirring and held at that temperature for approximately 60 minutes. The hot poly(vinyl alcohol) solution was cooled to approximately 60° C. and transferred into a 60 mL polypropylene syringe. The polypropylene syringe and contents were placed in an aluminum block heater previously warmed to 60° C. and dispensed into 2.0 cm$^2$ PETG cathode housing containing the silver chloride/polyisobutylene/carbon black electrode and electrically conductive adhesive tape, such as a pressure sensitive tape composed of polyisobutylene and carbon black. The filled PETG housing was covered with a polyethylene terephthalate (PET) release liner and the samples were placed in a freezer at −35° C. for approximately 24 hours. The frozen hydrogels were allowed to warm to ambient temperature to provide a cathode hydrogel containing cetylpyridinium chloride as an antimicrobial additive. The pH of the cathode hydrogel was 4.5.

Samples of the hydrogel formulations of Formulations 2 and 3 were prepared using the same technique except that the percentages of each of the components was as given in the above table.

The following media were used in the tests:
Trypticase Soy Agar (TSA) w/Lecithin and Polysorbate 80, Difco code No. 0553-17-2, or equivalent
Sabouraud Dextrose Agar (SDA), Difco Code No. 0305-17-3, or equivalent
Trypticase Soy Agar (TSA), BBL 11043, or equivalent
Phosphate Buffer, BBL No. 11544 or equivalent with the additional of 0.1% Polysorbate 80, BBL No. 11925 or equivalent Preparation of Standard Inocula Suspensions of inocula were made for each of the six challenge organisms in accordance with a standard procedure and only cultures with less than five passes were used. The suspensions were adjusted to approximately $1.0 \times 10^8$ colony forming units (CFU)/ml in accordance with a standard procedure. Immediately before inoculation, the inocula concentrations were confirmed by the Pour Plate Method (see the description provided in the U.S. Pharmacopeia 1995 and the publication *Biology of Microorganisms,* 3$^{rd}$ Ed. 1979, the contents of which are incorporated by reference).

The Pour Plate Method used Trypticase Soy Agar (TSA) for bacteria and Sabouraud Dextrose Agar (SDA) for yeast and mold. The TSA plates were incubated at 30–35° C. for 48–72 hours. The SDA plates inoculated with *A. niger* were incubated at 20–25° C. for 3 days. The SDA plates inoculated with *C. albicans* and Cladosporium species were incubated at 20–25° C. for 5–7 days. After incubation, the colonies were enumerated. The average colonies counted between the triplicate plates was multiplied by the dilution factor to obtain the number of organisms per system.

Sample Testing Procedure

To test the samples, the protective release liners were removed from reservoir housings under aseptic conditions. Each hydrogel formulation was inoculated with 6 L of the microorganism suspension (approximately $6.0 \times 10^5$ CFU/housing). Immediately after inoculation, the release liner was replaced and the inoculated housing was returned to the original package, which was sealed using a heat sealer. Resealed packages containing the inoculated housings were incubated at 20–25° C. Three replicate inoculated housings were analyzed at 0 hours, and at 2, 7, 14, 21, and 28 days after inoculation. This procedure was repeated for each of the six microorganisms tested. In order to evaluate the samples, each hydrogel was analyzed by first removing it from the package and the housing, placing it into a screw-capped tube containing 5.4 mL of Phosphate Buffer with 0.1% Polysorbate 80. Each tube was vortexed for 2 minutes. Using the Pour Plate Method, serial dilutions of the extract were plated on TSA with Lecithin and Polysorbate 80 for all bacteria, and on SDA for the yeast and mold. The plates were then incubated and enumerated in the manner discussed above.

The results of the tests set forth in Tables 1–3 which indicate that the cathodic hydrogel formulations containing 0.01%, 0.02% and 0.03% cetylpyridinium chloride meet the antimicrobial preservative efficacy requirements as stated in the US Pharmacopoeia 23 Microbiological Tests <51> *Antimicrobial Preservatives-Effectiveness* which are: 1) the concentrations of viable bacteria are reduced by a minimum of 3 logs after 14 days with no increase thereafter, and 2) the concentrations of viable yeast and molds remain at or below the initial concentrations throughout the 28-day study.

At all three concentrations of cetylpyridinium chloride, the viable microbial counts of all the challenge bacteria and yeast were reduced by Day 2 of the study, to less than the lowest detectable levels of the assay which is 10 CFU/housing. At a concentration of 0.03% CPC, the viable mold counts were also reduced to less than 10 CFU/housing by Day 2 of the study. At a concentration of 0.02% CPC, less than 0.1% of *A. niger* survived by Day 2; and Cladosporium species was reduced to less than 10 CFU/housing. At a concentration of 0.01% CPC, *A. niger* was reduced to less than 10 CFU/housing, and Cladosporium species was reduced to less than 0.1% by Day 14.

Further analysis of the experimental results indicate that the cathodic hydrogel formulations containing 0.01%, 0.02% and 0.03% cetylpyridinium chloride also satisfy the antimicrobial preservative requirements for topical preparations as stated in the British Pharmacopoeia which are: 1) The viable bacterial count was reduced by a minimum of three logs at the 48 hour time point with no recovery of the test bacteria at 7 day time point or thereafter, and 2) the viable fungal count was reduced by a minimum of two logs at the 14 day time point with no increase of the test fungi at the 28 day time point.

In addition, the cathodic hydrogel formulations containing 0.01%, 0.02%, and 0.03% cetylpyridinium chloride also satisfy the antimicrobial preservative requirements for topical preparations as stated in the Criteria A of the European Pharmacopoeia which are: 1) The viable bacteria count was reduced by at least two log and three log at the Day 2 and Day 7 time points respectively with no increase thereafter, 2) the viable fungal count was reduced by a minimum of two logs at the Day 14 time point with no increase of the test fungi at the Day 28 time point.

TABLE 1

| Organism | ATCC | Initial Sample Concentration[b] CFU[c]/System | 0 Hour[d] CFU/System | Day 2 CFU/System | Day 7 CFU/System | Day 14 CFU/System | Day 21 CFU/System | Day 28 CFU/System |
|---|---|---|---|---|---|---|---|---|
| *S. aureus* | 6538 | $9.0 \times 10^5$ | $<10^3$ | <10 | <10 | <10 | <10 | <10 |
| *E. coli* | 8739 | $7.8 \times 10^5$ | $<10^3$ | <10 | <10 | <10 | <10 | <10 |
| *P. aeruginosa* | 9027 | $1.0 \times 10^6$ | $<10^3$ | <10 | <10 | <10 | <10 | <10 |
| *C. albicans* | 10231 | $7.8 \times 10^5$ | $2.0 \pm 2.0 \times 10^3$ | <10 | <10 | <10 | <10 | <10 |
| *A. niger* | 16404 | $7.8 \times 10^5$ | $3.2 \pm 0.2 \times 10^4$ | $1.1 \pm 0.2 \times 10^2$ | $27 \pm 9$ | <10 | <10 | <10 |
| Cladosporium sp.[e] | N/A[f] | $9.0 \times 10^5$ | $3.1 \pm 0.1 \times 10^4$ | <10 | <10 | $1.6 \pm 0.5 \times 10^2$ | <10 | <10 |

Formulation: USP Purified Water (80.28%), washed polyvinyl alcohol (19.00%), sodium chloride, USP (0.10%), trisodium citrate (0.37%), citric acid, USP (0.24%), cetylpyridinium chloride (0.01%)
[b]Initial Sample Concentration: the baseline value to determine all subsequent changes in the organism concentration at various time points
[c]CFU: colony forming units
[d]0 Hour: Plate count immediately after inoculation. This count is not representative of the inoculation concentration because of possible immediate action of the antimicrobial
[e]Environmental Isolate: Isolated from cathode hydrogels without antimicrobial
[f]N/A: Not Applicable

TABLE 2

| Organism | ATCC | Initial Sample Concentration[b] CFU[c]/System | 0 Hour[d] CFU/System | Day 2 CFU/System | Day 7 CFU/System | Day 14 CFU/System | Day 21 CFU/System | Day 28 CFU/System |
|---|---|---|---|---|---|---|---|---|
| *S. aureus* | 6538 | $9.0 \times 10^5$ | $<10^3$ | <10 | <10 | <10 | <10 | <10 |
| *E. coli* | 8739 | $7.8 \times 10^5$ | $<10^3$ | <10 | <10 | <10 | <10 | <10 |
| *P. aeruginosa* | 9027 | $1.0 \times 10^6$ | $<10^3$ | <10 | <10 | <10 | <10 | <10 |
| *C. albicans* | 10231 | $7.8 \times 10^5$ | $<10^3$ | <10 | <10 | <10 | <10 | <10 |
| *A. niger* | 16404 | $7.8 \times 10^5$ | $<10^3$ | $30 \pm 22$ | <10 | <10 | <10 | <10 |
| Cladosporium sp.[e] | N/A[f] | $9.0 \times 10^5$ | $<10^3$ | <10 | <10 | <10 | <10 | <10 |

Formulation: USP Purified Water (80.28%), washed polyvinyl alcohol (19.00%), sodium chloride, USP (0.10%), trisodium citrate (0.37%), citric acid, USP (0.24%), cetylpyridinium chloride (0.01%)
[b]Initial Sample Concentration: the baseline value to determine all subsequent changes in the organism concentration at various time points
[c]CFU: colony forming units
[d]Plate count immediately after inoculation. This count is not representative of the inoculation concentration because of possible immediate action of the antimicrobial
[e]Environmental Isolate: Isolated from cathode hydrogels without antimicrobial
[f]N/A: Not Applicable

TABLE 3

| Organism | ATCC | Initial Sample Concentration[b] CFU[c]/System | 0 Hour[d] CFU/System | Day 2 CFU/System | Day 7 CFU/System | Day 14 CFU/System | Day 21 CFU/System | Day 28 CFU/System |
|---|---|---|---|---|---|---|---|---|
| *S. aureus* | 6538 | $9.0 \times 10^5$ | $<10^3$ | <10 | <10 | <10 | <10 | <10 |
| *E. coli* | 8739 | $7.8 \times 10^5$ | $<10^3$ | <10 | <10 | <10 | <10 | <10 |
| *P. aeruginosa* | 9027 | $1.0 \times 10^6$ | $<10^3$ | <10 | <10 | <10 | <10 | <10 |
| *C. albicans* | 10231 | $7.8 \times 10^5$ | $<10^3$ | <10 | <10 | <10 | <10 | <10 |

TABLE 3-continued

| Organism | ATCC | Initial Sample Concentration[b] CFU[c]/System | 0 Hour[d] CFU/System | Day 2 CFU/System | Day 7 CFU/System | Day 14 CFU/System | Day 21 CFU/System | Day 28 CFU/System |
|---|---|---|---|---|---|---|---|---|
| A. niger | 16404 | $7.8 \times 10^5$ | $<10^3$ | <10 | <10 | <10 | <10 | <10 |
| Cladosporium sp.[e] | N/A[f] | $9.0 \times 10^5$ | $<10^3$ | <10 | <10 | <10 | <10 | <10 |

Formulation: USP Purified Water (80.26%), washed polyvinyl alcohol (19.00%), sodium chloride, USP (0.10%), trisodium citrate (0.37%), citric acid, USP (0.24%), cetylpyridinium chloride (0.03%).
[b]Initial Sample Concentration: the baseline value to determine all subsequent changes in the organism concentration at various time points.
[c]CFU: colony forming units
[d]0 Hour: Plate count immediately after inoculation. This count is not representative of the inoculation concentration because of possible immediate action of the antimicrobial
[e]Environmental Isolate: Isolated from cathode hydrogels without antimicrobial
[f]N/A: Not Applicable

EXAMPLE 2

To further illustrate the antimicrobial effectiveness of the cetylpyridinium salt of the present invention, cathodic hydrogel formulations were made containing 0.08% cetylpyridinium chloride with various microorganisms including bacteria, yeast and mold. The organisms used were S. aureus, E. coli, P. aeruginosa, C. albicans and A. niger as well as four environmental fungal isolates. The test methods followed were the same as those discussed above with respect to the U.S. Pharmacopoeia, the British Pharmacopoeia and the European Pharmacopoeia.

The microorganisms used were as follows:

| | |
|---|---|
| Bacteria | S. aureus ATCC No. 6538 |
| | E. coli ATCC No. 8739 |
| | P. aeruginosa ATCC No. 9027 |
| Yeast | C. albicans ATCC No. 10231 |
| Mold | A. niger ATCC 16404 |

Environmental Isolates

Penicillium species (environmental isolate)

Cladosporium species (environmental isolate)

Aspergillus species (environmental isolate)

Cryptococcus albidus (environmental isolate)

The formulation used in the test was as follows:

Formulation 4:

Purified water, USP (84.21%), Washed PVOH (15.00%), Citric Acid, USP (0.24%), Trisodium Citrate Dihydrate, USP (0.37%), Sodium Chloride, USP (0.10%), Cetylpyridinium Chloride (0.08%), pH 4.5

Samples of the formulation were prepared in a manner similar to the procedure set forth above for Example 1.

The following media were used in the tests:

Trypticase Soy Agar (TSA) with Lecithin and polysorbate 80, BBL Code No. 4311764, or equivalent Sabouraud Dextrose Agar (SDA), BBL Code No. 4311584, or equivalent Trypticase Soy Broth (TSB), BBL Code No. 4311768, or equivalent Saline TS containing 0.05% polysorbate 80

Fluid A (USP): 0.1% Bacto-Peptamin, Difco Code No. 0905-01, or equivalent

Fluid D (USP): 0.1% Bacto-peptamin, Difco Code No. 0905-01, or equivalent, 0.1% Polysorbate 80, Difco Code No. x257-07, or equivalent Standardizaing Challenge Inocula Microbial cultures were prepared as described in the U.S., British and European Pharmacopoeias. In particular, the bacterial cultures were subcultured into TSB and incubated at 30–35° C. for 18–24 hours. the yeast cultures (C. albicans and Cryptococcus albidus) were subcultured into TSB and incubated at 20–25° C. for 48 hours while shaking (aerated to obtain a higher concentration of organism). Following incubation, each suspension was washed by centrifugation at 10,000 rpm for 10 minutes at 4° C. The cultures were washed twice with sterile distilled water and the pellets were resuspended in sterile water. The prepared suspension concentrations were determined turbidimetrically by reading the absorbance value at a wavelength of 530 nm. The suspension concentrations were adjusted to yield approximately $10^8$ colony forming units (CFU) per milliliter and were used immediately thereafter.

Fungal (mold) spores were grown as described in the U.S. Pharmacopoeia. In particular, the cultures of A. niger, Cladosporium species, Aspergillus species, and Penicillium species were grown on the surface of SDA plates at 20–25° C. for 1 week or until heavy sporulation was obtained. Following the incubation, each fungal culture was harvested in sterile saline TS containing 0.05% polysorbate 80. The number of CFU/mL in the suspension was determined by Pour Plate Method in SDA. Spore counts were adjusted to approximately $10^8$ CFU per milliliter.

Testing Procedure

In order to inoculate the samples, the following procedure was followed for all microorganisms. Using an aseptic technique in a protected environment, thirty samples of hydrogel formulation were placed into 45 mm diameter petri dishes (one gel per dish). Protective release liners were removed from the gels and stored aseptically in petri dishes. Each housing was inoculated with three 3 μL aliquots of microorganism suspension (approximately $10^6$ CFU/housing). Inoculation concentrations were determined using Pour Plate Method at the beginning, middle, and end of the inoculation procedure. Immediately after inoculation, the petri dishes containing inoculated housings were placed into their original foil lined pouches to protect the sample from light and moisture loss. Excess air volume inside the foil pouches was removed by pressing gently on both side of the foil pouch while ensuring that the pouches did not contact the inoculum on the surface of the hydrogels. Pouches were sealed using a heat sealer. After 24 hours, each foil pouch was cut open and the release liner was replaced on the inoculated surface of each sample (to simulate the product storage condition) and the pouches were resealed with the heat sealer. Resealed pouches containing the inoculated housings were stored at 20–25° C. for a duration of 28 days.

Five inoculated housing per organism were recovered at 2, 7, 14, 21 and 28 days subsequent to inoculation.

To analyze the housings, each of the five inoculated housings with release liners in place, were removed from their pouches and placed into five screw-capped tubes each containing 20 mL of Fluid D (USP). Tubes with samples and release lines were placed onto a horizontal shaker and the contents were agitated at approximately 200 RPM for 30 minutes. The tubes were removed from the shaker and vortexed at high speed for 1 minute. Serial ten fold dilutions were made for each tube and aliquots cultured using the Pour Plate Method with 20–30 mL of nutrient medium: TSA with lecithin and polysorbate 80 for bacteria and SDA for fungi. Bacterial cultures were incubated at 30–35° C. for 48 hours and the fungal cultures were incubated at 20–25° C. for 3–5 days.

The results are summarized in Table 4. As can be determined from Table 4, the viable bacterial counts for *S. aureus, E. coli* and *P. aeruginosa* and viable yeast counts for *C. albicans* and *Cryptococcus albidus* (environmental isolate) on the surface of the inoculated samples were reduced to less than 10 CFU/housing, which is the maximum sensitivity of the assay method, upon 2 days of exposure and thereafter (a decrease in excess of 4 logs). The viable mold counts for *A. niger* and the environmental isolates (Cladosporium species, Penicillium species and Aspergillus species) on the inoculated samples were reduced by greater than 3 logs by day 2 and no increase by day 28. The results of the tests indicate that the cathodic hydrogel formulation containing 0.08% cetylpyridinium chloride meets the antimicrobial preservative efficacy requirements discussed above in the U.S., British and European Pharmacopoeias.

COMPARATIVE EXAMPLES

For purposes of comparison, Tables 5 and 6 provide the results of tests of hydrogel samples (the formulations being described below each Table) without cetylpyridinium chloride over a twelve month period. Fungal growth was observed in these formulations as shown in the Tables.

TABLE 4

| Organisms[b] | Time Exposure | | | | | |
|---|---|---|---|---|---|---|
| | Day 0 | Day 2 | Day 7 | Day 14 | Day 21 | Day 28 |
| S. aureus ATCC 6538 | $2.7 \pm 0.3 \times 10^6$ | <10[d] | <10 | <10 | <10 | <10 |
| E. Coli ATCC 8739 | $4.3 \pm 0.4 \times 10^6$ | <10 | <10 | <10 | <10 | <10 |
| P. aeruginosa ATCC 9027 | $1.1 \pm 0.2 \times 10^6$ | <10 | <10 | <10 | <10 | <10 |
| C. albicans ATCC 10231 | $2.0 \pm 0.5 \times 10^6$ | <10 | <10 | <10 | <10 | <10 |
| A. niger ATCC 16404 | $4.4 \pm 0.9 \times 10^5$ | $3.8 \pm 0.8 \times 10^2$ | $0.8 \pm 1.3 \times 10^1$ | $2.9 \pm 0.9 \times 10^2$ | $6.2 \pm 2.9 \times 10^1$ | $6.6 \pm 2.4 \times 10^1$ |
| Cladosporium sp.[c] | $2.9 \pm 0.5 \times 10^5$ | <10 | <10 | $2.6 \pm 1.1 \times 10^1$ | $2 \pm 4.5$ | <10 |
| Cryptococcus albidus[c] | $2.4 \pm 0.1 \times 10^5$ | <10 | <10 | <10 | <10 | <10 |
| Penicillium sp.[c] | $7.8 \pm 1.4 \times 10^6$ | <10 | <10 | $3.8 \pm 1.8 \times 10^1$ | $0.8 \pm 0.8 \times 10^1$ | <10 |
| Aspergillus sp.[c] | $2.6 \pm 0.8 \times 10^6$ | <10 | <10 | $1.6 \pm 0.9 \times 10^1$ | $2.2 \pm 1.3 \times 10^1$ | <10 |

Formulation: USP Purified Water (84.21%), Washed PVOH (15.00%), Citric Acid, USP (0.24%), Trisodium Citrate, USP (0.37%), Sodium Chloride, USP (0.10%), Cetylpyridinium chloride (0.08%)
[b]Organism Concentrations: colony forming units (CFU)/system
[c]Environmental isolates
[d]Maximum sensitivity of the assay method

TABLE 5

| Organisms[b] | Day 0 | Day 7[d] | Day 15 | Month 1[e] | Month 3 | Month 6[f] | Month 9[g] | Month 12[h] |
|---|---|---|---|---|---|---|---|---|
| C. albicans ATCC 10231 | $4.6 \pm 1.2 \times 10^2$ | <10[c] | <10 | <10 | <10 | <10 | <10 | <10 |
| A. niger ATCC 16404 | $6.3 \pm 0.3 \times 10^2$ | $6.3 \pm 0.6 \times 10^2$ | $5.7 \pm 1.2 \times 10^2$ | $4.6 \pm 1.0 \times 10^2$ | $4.8 \pm 1.9 \times 10^2$ | $1.5 \pm 1.3 \times 10^2$ | $2.5 \pm 0.7 \times 10^1$ | $9.7 \pm 0.7 \times 10^1$ |

Formulation: USP Purified Water (87.29%), Washed PVOH (12.00%), Citric Acid, USP (0.24%), Trisodium Citrate, USP (0.37%), Sodium Chloride, USP (0.10%) PH 4.0
[b]Fungal Concentrations: colony forming units (CFU)/system; n = 4 or 3
[c]Maximum sensitivity of the assay method
[d]One Penicillium sp. at $10^4$ CFU level was detected from one of the four units inoculated with *A. niger ATCC 16404*
[e]One Penicillium sp. at $10^5$ CFU level was detected from two of the four units and one Aspergillus sp. at $10^4$ CFU level was detected from the other two units inoculated with *A. niger ATCC 16404* (no contaminants detected from the re-tested samples)

TABLE 6

| Organisms[b] | Day 0 | Day 7 | Day 15 | Month 1[c] | Month 3 | Month 6[e] | Month 9 | Month 12 |
|---|---|---|---|---|---|---|---|---|
| Yeast | $1.1 \pm 0.6 \times 10^2$ | $<10^d$ | <10 | <10 | <10 | <10 | <10 | TBD[f] |
| Penicillium sp. | $1.1 \pm 0.2 \times 10^3$ | $8.7 \pm 11.0 \times 10^1$ | $1.0 \pm 1.0 \times 10^1$ | $1.0 \pm 1.7 \times 10^2$ | $3.6 \pm 6.2 \times 10^2$ | <10 | <10 | TBD |
| Cladosporium sp. | $1.0 \pm 0.3 \times 10^2$ | <10 | <10 | <10 | $1.1 \pm 1.8 \times 10^2$ | <10 | <10 | TBD |

Formulation: USP Purified Water (87.29%), Washed PVOH (12.00%), Citric Acid, USP (0.24%), Trisodium Citrate, USP (0.37%), Sodium Chloride, USP (0.10%) pH 4.0
[b]Yeast and Cladosporium sp. were isolated from the manufacturing environment. Penicillium sp. was isolated from gel inoculated with *A. niger* ATCC 16404 in the previous experiment
Fungal concentrations: colony forming units (CFU)/system; n = 3 except the 6 month timepoint (n = 6)

EXAMPLE 3

To illustrate the compatibility of cetylpyridinium chloride with polyethylene terephthalate modified with cyclohexane dimethylol (obtained from Easan Chemical Products, Inc. under the designation KODAR PETG copolyester 6763) and using a composite cathodic electrode composed of polyisobutylene, carbon and silver chloride, the following formulation was prepared into a hydrogel.

TABLE 7

| Raw Material | WT % |
|---|---|
| Purified Water, USP | 84.215 |
| Citric acid | 0.240 |
| Trisodium citrate dihydrate | 0.370 |
| Sodium chloride | 0.100 |
| Washed poly(vinyl alcohol) Moviol 66- | 15.000 |
| Cetylpyridinium chloride | 0.075 |

The hydrogel formulation was prepared by adding 84.2 g of purified water, USP, 0.24 g of citric acid, 0.37 g of trisodium citrate dihydrate, 0.10 g of sodium chloride and 15.0 g of washed poly(vinyl alcohol) into a 250 mL jacketed glass beaker. A rubber stopper equipped with a nitrogen inlet, powder addition funnel, thermocouple thermometer and a stainless steel stirring shaft with a Delrin paddle was inserted into the mouth of the beaker. The mixture was stirred (Arrow 850, speed setting=1 to 2) while warming to 90–95 C. and held at that temperature for 70 minutes. The citrate buffer solution of poly(vinyl alcohol) was cooled at 50° C. and 0.075 g of cetylpyridinium chloride was added to the beaker. The mixture was stirred for 15 minutes and the cetylpyridinium chloride was completely dissolved. The polymer solution was transferred into a 60 mL polypropylene syringe that was previously warmed to 55° C. with an aluminum block heater and dispensed into thermoformed lower housings of the PETG material (which contained a composite cathode composed of 29% by weight polyisobutylene, 2.5% by weight carbon and 68% by weight silver chloride and having an area density of approximately 0.35 mg/cm$^2$) with a Multicore solder paste dispenser. The filled cathode hydrogel formation samples were covered with a siliconized polyethylene terephthalate release liner and the filled systems were stored in the −20° C. freezer for 18 hours and allowed to warm to ambient temperature on the bench top. The crosslinked hydrogel formation samples, polymeric material housing and polyethylene terephthalate release liner were weighed and individually packaged in a sealed Surlyn lined foil pouch.

The cathode hydrogel formation samples were removed from the foil pouches after storage at 4, 25 and 40° C. for 1, 4, 8, 12, 24 and 48 weeks. The cathode hydrogel formulation samples were extracted with a mobile phase composed of 60% water/40% acetonitrile and the cetylpyridinium chloride (CPC) content was determined by HPLC analysis. The results of the test are set forth in Table 8 as follows.

TABLE 8

| Time (weeks) | wt % CPC (4 C.) | wt % CPC (25 C.) | wt % CPC (40 C.) |
|---|---|---|---|
| 0 | 0.075 | 0.075 | 0.075 |
| 1 | 0.084 | 0.082 | 0.080 |
| 4 | 0.070 | 0.077 | 0.064 |
| 8 | 0.071 | 0.073 | 0.067 |
| 12 | 0.058 | 0.061 | 0.053 |
| 24 | 0.055 | 0.059 | 0.052 |
| 48 | 0.055 | 0.053 | 0.043 |

To understand the foregoing results more completely, it is noted that the weight of the cathode hydrogel is 0.64 g. Therefore, the content of cetylpyridinium chloride (based on 0.075 wt % CPC in the hydrogel) is 0.48 mg CPC/hydrogel which corresponds to 0.75 mg CPC/g hydrogel. After 48 weeks at 4, 25° C. and 40° C., the concentration of CPC in the cathode hydrogel decreased to 0.055 wt %, 0.053 wt % and 0.043 wt %, respectively. The concentration of CPC in the cathode hydrogel formation after 48 weeks at 4° C., 25° C. and 40° C. was 0.55, 0.53, 0.43 mg CPC/g hydrogel. The amount of CPC lost to the composite cathode after 48 weeks at 4, 25 and 40° C. was 0.20, 0.22 and 0.32 mg CPC/g hydrogel, respectively. The area of the AgCl/PIB composite cathode is 2.33 cm$^2$. The amount of CPC lost after 48 weeks at 4° C., 25° C. and 40° C. based on contact with 1.0 cm$^2$ of AgCl/PIB composite was calculated to be 0.086, 0.094 and 0.137 mg CPC/g hydrogel/cm$^2$ composite, respectively.

Subsequent extraction experiments showed that the cetylpyridinium chloride was lost primarily to the composite cathode. As noted above, one potential solution to this situation is to provide an anion exchange membrane, such as a SYBRON or RAIPORE anion exchange membrane, between the electrode and the contents of the reservoir so that the cetylpyridinium cations will not penetrate through such membrane and therefore will not contact the cathodic electrode.

ABSORPTION DATA

To illustrate absorption of cetylpyridinium chloride and benzyl chloride by additional polymeric materials, two sets of solutions were prepared. One set of sample solutions was composed of 0.01% sodium chloride, 0.24% citric acid, 0.37% sodium citrate, 0.03% benzoic acid (BA) and, 76% water. This gave a concentration of 397 μg BA/ml which is at the upper end of the assay range in the experimental method for BA, but is one-tenth that normally used in hydrogel formulations.

The other set of sample solutions contained CPC dissolved in water at a concentration of 58.1 μg/m which is near the middle of the assay range for CPC.

The following polymeric materials were tested:

EXX-216 TiO$_2$-filled polypropylene (obtained from Exxon Chemical Co.)

EXX-210 Polypropylene (0.1 millimeter thickness)

ACLAR Laminate obtained from Techniplex consisting of 0.13 millimeter polyvinyl chloride (PVC)/0.05 millimeter polyethylene/0.15 millimeter ACLAR (a fluorohalocarbon film)

For the tests, 150 cm$^2$ of test material was cut into small pieces and immersed in 50 ml of test solution. One sample of each material was prepared in a 100 ml glass extraction bottle for storage at 25° C. and another for storage at 40° C. Because the PVC and ACLAR® sides of the trilaminate test material would be expected to exhibit different properties a second set of samples was prepared with two pieces of the ACLAR® laminated to a piece of electrically conductive adhesive tape so that only the ACLAR® side was exposed to the test solution.

Since the electrically conductive adhesive tape might also absorb the antimicrobial agents, a control was prepared by sandwiching the tape between glass microscope slides. Another control was simply glass microscope slides. All samples exposed the same proportion of test surface area to ml of test solution. All samples using the electrically conductive adhesive tape had approximately the same area of tape exposed per ml of solution.

The prepared sample bottles were weighed and stored at 25° C. and at 40° C. for eight weeks. At t=1 day, 1 week, 2 weeks, 4 weeks, 8 weeks, samples were equilibrated to room temperature and weighted. Any samples that had lost more than 0.1 g during the previous storage period were returned to the proper weight by addition of water before sampling. Samples were kept small to minimize the effect on the remaining time points. New weights were recorded before returning the samples to the chambers each time. At the end of the study the sample pieces were removed from the solutions for visual observation.

The results of the tests are provided in Table 9. In the Table, "ACLAR (clear)" refers to pieces of the ACLAR sample completely immersed in solution. "ACLAR (laminate)" refers to ACLAR laminated with the electrically conductive adhesive tape so that only the ACLAR side was exposed. The same nomenclature was used with the glass slide examples. In addition, it is noted that the benzoic acid tests were terminated after 4 weeks because no changes in concentration had been detected for any of the samples at either temperature.

TABLE 9

CPC Solution 58.08 ug/ml

| # | Material | Temp | T = 0 | 1 Day | 1 Week | 2 Weeks | 4 Weeks | 8 Weeks |
|---|---|---|---|---|---|---|---|---|
| 1 | Control 4C | 4 | 58.08 | 56.87 | 56.13 | 54.33 | 55.58 | 55.68 |
| 2 | Control 25C | 25 | 58.08 | 56.94 | 57.25 | 55.29 | 56.20 | 55.29 |
| 3 | Control 40C | 40 | 58.08 | 56.94 | 57.32 | 56.50 | 56.80 | 57.40 |
| 4 | EXX-210 (clear) 25C | 25 | 58.06 | 54.00 | 56.61 | 54.80 | 56.28 | 54.28 |
| 5 | EXX-210 (clear) 40C | 40 | 58.08 | 53.17 | 51.80 | 54.68 | 53.14 | 54.92 |
| 6 | EXX-216 (white) 25C | 25 | 58.08 | 54.32 | 58.82 | 54.53 | 56.28 | 56.91 |
| 7 | EXX-216 (white) 40C | 40 | 58.08 | 55.10 | 58.08 | 56.26 | 55.43 | 52.64 |
| 8 | ACLAR (clear) 25C | 25 | 58.08 | 63.62 | 55.65 | 56.77 | 67.17 | 56.50 |
| 9 | ACLAR (clear) 40C | 40 | 58.08 | 54.22 | 57.90 | 54.83 | 56.25 | 53.89 |
| 1 | ACLAR (laminated) 25C | 25 | 58.08 | 57.40 | 57.17 | 57.02 | 56.60 | 55.86 |
| 1 | ACLAR (laminated) 40C | 40 | 58.08 | 57.17 | 57.68 | 58.53 | 52.79 | 50.99 |
| 12 | Glass Slides 40C | 40 | 58.08 | 52.36 | 49.96 | 49.67 | 51.57 | 48.61 |
| 13 | Glass Slides (laminated) 40C | 40 | 58.08 | 52.64 | 52.51 | 50.75 | 49.32 | 48.88 |

Benzoic Acid Sol'n 397.25 ug/ml

| # | Material | Temp | T = 0 | 1 Day | 1 Week | 2 Weeks | 4 Weeks |
|---|---|---|---|---|---|---|---|
| 1 | Control 4C | 4 | 397.25 | 396.96 | 399.35 | 397.62 | 399.01 |
| 2 | Control 25C | 25 | 397.25 | 397.26 | 398.32 | 398.65 | 401.43 |
| 3 | Control 40C | 40 | 397.25 | 396.37 | 398.17 | 398.95 | 400.14 |
| 4 | EXX-210 (clear) 25C | 25 | 397.25 | 396.22 | 397.15 | 394.97 | 395.29 |
| 5 | EXX-210 (clear) 40C | 40 | 397.25 | 397.26 | 394.50 | 395.56 | 397.55 |
| 6 | EXX-216 (white) 25C | 25 | 397.25 | 395.48 | 396.12 | 396.59 | 396.58 |
| 7 | EXX-216 (white) 40C | 40 | 397.25 | 396.22 | 396.26 | 397.33 | 396.91 |
| 8 | ACLAR (clear) 25C | 25 | 397.25 | 397.70 | 398.32 | 397.92 | 397.71 |
| 9 | ACLAR (clear) 40C | 40 | 397.25 | 398.30 | 397.59 | 397.77 | 400.79 |
| 10 | ACLAR (laminated) 25C | 25 | 397.25 | 398.30 | 397.00 | 398.65 | 396.74 |
| 11 | ACLAR (laminated) 40C | 40 | 397.25 | 397.55 | 396.70 | 397.92 | 396.42 |
| 12 | Glass Slides 40C | 40 | 397.25 | 400.97 | 398.91 | 399.83 | 399.17 |
| 13 | Glass Slides (laminated) 40C | 40 | 397.25 | 400.52 | 397.73 | 398.65 | 398.85 |

From test results and visual observations, it is noted that all the CPC test materials showed some loss of CPC compared to the controls. The largest losses were the control samples containing the glass slides. Results were similar for glass with or without the electrically conductive adhesive tape.

Additional absorption data for talc filled polypropylene, PETG and siliconized PET release liner were obtained using cathode solutions containing cetylpyridinium chloride (CPC).

The solutions and the samples are described as follows:
Preparation of Cathode Solution—1.0 mg/ml CPC Into a 1000 mL volumetric flask were added 1.379 g citric acid, 6.321 g trisodium citrate dihydrate, 1.149 g sodium chloride, and 1.0 g cetylpyridinium chloride. The flask was then filled to the mark with millipore water and stirred for approximately 15 minutes until all of the salts had completely dissolved.

Preparation of Cathode Solution—0.1 mg/ml CPC

Into a 500 mL volumetric flask was added 50 mL of the 1.0 mg/ml CPC solution via a 50 mL pipette. The flask was then filled to the mark with millipore water and the contents stirred until homogeneous.

Preparation of CPC/Talc filled Polypropylene Samples

Talc filled polypropylene sheet stock (available under the designation Proprint) was die cut into 2 cm$^2$ discs. Into each glass vial was placed 24 discs. The weight of 24 discs was approximately 1.0 gram. Into each vial was measured 2 mL of the proper solution via a repeating pipette. Eighteen samples per solution were prepared. The weight of all the vials was recorded at t=0. The samples were stored in an environmental chamber at 25° C.

Preparation of CPC/PETG Samples

Into each 125 mL glass media bottle was added approximately 9.5 g of blue trilaminate lower housings. The housings were cut into small pieces to allow them to fit through the neck of the jar. Into each jar was then measured 16.6 mL of the proper CPC solution. Three samples of each solution concentration were prepared. The weight of the PETG placed in each sample was recorded at t=0. The samples were then placed on a shaker at ambient temperature.

Preparation of CPC/PET Samples

Into each 125 mL glass media bottle was added approximately 8.2 g of siliconized PET release liner. The release liner was cut into smaller pieces to ensure passage through the neck of the jar. Into each jar was then measured 16.6 mL of the proper CPC solution. Three samples of each solution concentration were prepared. The weight of the PET placed in each sample was recorded at t=0. The samples were then placed on the shaker at ambient temperature.

Preparation of Control Solutions

The original CPC solutions prepared for these compatibility studies were used as the control solutions. They were stored in glass volumetric flasks at ambient temperature.

The CPC control solutions and test samples were removed from the environmental chambers and shaker after 24 hours, 1, 2, 4, 8, and 16 weeks. The Proprint samples were weighed to determine if any evaporative water loss had occurred. If this was the case, then water was added to the vial to equal the weight at the previous time point. The PET and PETG samples were resealed and returned to the shaker after analysis, while the Proprint samples were discarded after each time point. The test solutions were sampled and analyzed for CPC content by HPLC analysis.

The results are set forth in Tables 10 and 11 and represent the actual amount of CPC absorbed per gram of substrate. These values were determined by calculating the mg CPC lost/mL of solution. This value was multiplied by the total solution volume to obtain total mg of CPC lost. This was then divided by the total weight of the substrate in the sample to obtain mg CPC lost per gram of substrate.

TABLE 10

| mg of CPC absorbed per gram of Proprint | | |
|---|---|---|
| Weeks | 0.1 mg/ml CPC | 1.0 mg/ml CPC |
| 0 | 0.100 | 1.023 |
| 0.14 | 0.104 | 0.098 |
| 1 | 0.145 | 0.048 |
| 2 | 0.156 | 0.101 |
| 4 | 0.72 | 0.271 |

TABLE 10-continued

| mg of CPC absorbed per gram of Proprint | | |
|---|---|---|
| Weeks | 0.1 mg/ml CPC | 1.0 mg/ml CPC |
| 8 | 0.173 | 0.492 |
| 16 | 0.178 | 0.202 |

TABLE 11

| Mg of CPC Absorbed per gram of PETG and PET | | | | |
|---|---|---|---|---|
| Weeks | 0.1 mg/mL CPC-PET | 0.1 mg/mL CPC-PETG | 1.0 mg/mL CPC-PET | 1.0 mg/mL CPC-PETG |
| 1 = 0 concentration | 0.100 | 0.100 | 1.000 | 1.000 |
| 0.14286 | 0.062 | 0.018 | 0.046 | −0.022** |
| 1 | 0.157 | 0.023 | 0.052 | −0.079** |
| 2 | 0.176 | 0.022 | 0.123 | 0.087 |
| 4 | NPD* | 0.024 | 0.367 | −0.009** |
| 8 | 0.182 | 0.026 | 0.216 | 0.013 |
| 16 | 0.182 | 0.014 | 0.130 | −0.317** |

*No product determined.
**The negative values are due to a CPC concentration higher than the t = 0 concentration.

EXAMPLE 4

To illustrate the compatibility of cetylpyridinium chloride (CPC) with a silver chloride/carbon composite cathode and other housing materials, a cathode hydrogel was prepared and tested. The cathode hydrogel was prepared by adding 3.0 g of L-histidine and 148.84 g of purified water, USP into a 250 mL jacketed glass beaker. A Teflon coated magnetic spin bar was placed into the beaker and the L-histidine was completely dissolved. A pH electrode was placed into the aqueous L-histidine solution and the pH was adjusted to pH=4.5 by the dropwise addition of concentrated hydrochloric acid (1.968 g). Additional purified water, USP (8.032 g) was added to afford 200 g of the mixture. The magnetic spin bar was removed from the jacketed beaker and 38.0 g of washed poly(vinyl alcohol) was added to the beaker. A rubber stopper equipped with a thermocouple thermometer and a stainless steel stirring shaft with a Delrin paddle was inserted into the mouth of the jacketed beaker. The mixture was stirred while warming to 90° C. and held at that temperature for 70 minutes. The solution of poly(vinyl alcohol) was cooled to 60° C. and 0.16 g of cetylpyridinium chloride was added to the jacketed beaker. The mixture was stirred for approximately 10 minutes and the cetylpyridinium chloride was completely dissolved. The solution was transferred into a 60 mL polypropylene syringe that was previously warmed with an aluminum block heater to 60° C. and dispensed into lower housings composed of talc filled polypropylene (available under the designation Proprint) with a Multicore solder paste dispenser. The filled cathode hydrogel reservoirs were covered with a siliconized polyethylene terephthalate (PET) release liner and the filled systems were stored in a −20° C. freezer for 18 hours and allowed to warm to 4° C. for 2 hours and then allowed to warm to ambient temperature. The crosslinked hydrogel was removed from the hydrogel reservoir and weighed to determine the initial weight. The initial pH of the cathode hydrogel was 4.53. The samples were individually sealed in a Surlyn lined foil pouch and stored at 40° C.

At weeks 1, 4, 8, 12, 32 and 56, the hydrogels were removed from the lower housing and extracted with a mobile phase composed of 60% water/40% acrylonitrile and the cetylpyridinium chloride concentration was determined by HPLC analysis (AAM 1.443). The components of the lower housing were extracted separately to determine the quantity of cetylpyridinium chloride that had diffused into them and the results are provided in Table 12.

TABLE 12

| Time (weeks) | Hydrogel (wt % CPC) | Housing (wt % CPC) | PET Liner (wt % CPC) | AgCl/ECAT Laminate (wt % CPC) |
| --- | --- | --- | --- | --- |
| 0 | 0.086 | 0 | 0 | 0 |
| 1 | 0.076 | 0.001 | 0.000 | 0.005 |
| 4 | 0.058 | 0.002 | 0.002 | 0.012 |
| 8 | 0.049 | 0.001 | 0.002 | 0.015 |
| 12 | 0.043 | 0.001 | 0.002 | 0.017 |
| 32 | 0.043 | 0.002 | 0.003 | 0.017 |
| 56 | 0.043 | 0.002 | 0.004 | 0.014 |

Although the present invention has been described with reference to certain preferred embodiments, it is apparent that modifications and variations thereof may be made by those skilled in the art without departing from the scope of the invention as defined by the following claims.

What is claimed is:

1. A transdermal electrotransport drug delivery device comprised of an anode, a cathode and a source of electrical power electrically connected to the anode and the cathode, the cathode including a cathodic electrode and a cathodic reservoir comprised of a housing composed of a polymeric material and an aqueous medium in contact with the housing, said aqueous medium comprised of i) a drug or an electrolyte salt or a mixture thereof and ii) a cetylpyridinium salt in an amount sufficient to inhibit microbial growth in the aqueous medium wherein said polymeric material is compatible with the cetylpyridinium salt.

2. The transdermal electrotransport drug delivery device of claim 1 wherein the aqueous medium has a pH of from about 3 to about 7.5.

3. The transdermal electrotransport drug delivery device of claim 2 wherein the aqueous medium has a pH of from about 3.5 to about 6.5.

4. The transdermal electrotransport drug delivery device of claim 1 wherein the aqueous medium includes a buffer.

5. The transdermal electrotransport drug delivery device of claim 1 wherein the polymeric material is selected from the group consisting of polyethylene terephthalate, polyethylene terephthalate modified with cyclohexane dimethylol, polypropylene and mixtures thereof.

6. The transdermal electrotransport drug delivery device of claim 1 wherein the cathodic reservoir contains an aqueous medium of an electrolyte salt and is substantially drug free.

7. The transdermal electrotransport drug delivery device of claim 6 wherein the anode includes an anodic electrode and an anodic reservoir that contains a drug.

8. The transdermal electrotransport drug delivery device of claim 7 wherein the anodic reservoir contains fentanyl in a form that can be delivered when current flows from the source of electric power.

9. The transdermal electrotransport drug delivery device of claim 1 wherein the cetylpyridinium salt is a halide salt.

10. The transdermal electrotransport drug delivery device of claim 9 wherein the cetylpyridinium halide salt is cetylpyridinium chloride.

11. The transdermal electrotransport drug delivery device of claim 1 wherein the aqueous medium contains at least about 0.005% by weight of the cetylpyridinium salt.

12. The transdermal electrotransport drug delivery device of claim 11 wherein the aqueous medium contains from about 0.005% to about 2% by weight of the cetylpyridinium salt.

13. The transdermal electrotransport drug delivery device of claim 12 wherein the aqueous medium contains from about 0.01% to about 1% by weight of the cetylpyridinium salt.

14. The transdermal electrotransport drug delivery device of claim 1, including an anion exchange membrane between the cathodic electrode and the cathodic reservoir.

15. A process for transdermally delivering a drug to a patient by electrotransport from a drug delivery device comprised of an anode, a cathode and a source of electrical power electrically connected to the anode and the cathode, the anode including an anodic electrode and an anodic reservoir that contains a drug and the cathode including a cathodic electrode and a cathodic reservoir composed of a polymeric material and containing an aqueous medium comprised of i) an electrolyte salt and ii) a cetylpyridinium salt in an amount sufficient to inhibit microbial growth in the aqueous medium, said polymeric material being compatible with the cetylpyridinium salt, said process comprising providing electric current from the source of electrical power so that the drug is transdermally delivered to the patient by electrotransport from the anodic reservoir and so that cetylpyridinium ions are not transdermally delivered to the patient by electrotransport from the cathodic reservoir.

16. The process of claim 15 wherein the drug is fentanyl in a form that can be delivered when current flows from the source of electric power.

17. The process of claim 15 wherein the aqueous medium is a hydrogel comprised of at least about 0.005% by weight of the cetylpyridinium salt.

18. The process of claim 17 wherein the hydrogel comprises from about 0.005% to about 2% by weight of the cetylpyridinium salt.

19. The process of claim 18 wherein the hydrogel comprises from about 0.01% to about 1% by weight of the cetylpyridinium salt.

20. The process of claim 15 wherein the cetylpyridinium salt is cetylpyridinium chloride.

21. The process of claim 15 wherein substantially no drug is delivered from the cathodic reservoir when current flows from the source of electric power.

22. The process of claim 15 wherein the drug comprises fentanyl.

23. A process of preparing a transdermal electrotransport drug delivery device comprising preparing an aqueous medium comprised of i) a drug or an electrolyte salt or a mixture thereof and ii) a cetylpyridinium salt in an amount sufficient to inhibit microbial growth in the aqueous medium; and placing the aqueous medium in the cathodic reservoir of a device comprised of an anode, a cathode and a source of electrical power electrically connected to the anode and the cathode, the cathode including a cathodic electrode and a cathodic reservoir comprised of a housing composed of a polymeric material whereby the aqueous medium is in contact with the housing of the cathodic reservoir and wherein said polymeric material is selected so that it is compatible with the cetylpyridinium salt.

24. The process of claim 23 wherein the polymeric material is selected from the group consisting of polyethylene terephthalate, polyethylene terephthalate modified with cyclohexane dimethylol, polypropylene and mixtures thereof.

25. The process of claim 23 wherein the aqueous medium is substantially drug free.

26. The process of claim 23 wherein the cetylpyridinium salt is a halide salt.

* * * * *